United States Patent [19]

Hayakawa et al.

[11] Patent Number: 4,593,700

[45] Date of Patent: Jun. 10, 1986

[54] ULTRASONIC WAVE BLOOD FLOW METER

[75] Inventors: Yoshihiro Hayakawa, Sagamihara; Yasuhiro Nakamura, Tokyo; Ryobun Tachita; Tsutomu Yano, both of Kawasaki, all of Japan

[73] Assignee: Matsushita Electric Industrial Co., Ltd., Osaka, Japan

[21] Appl. No.: 647,489

[22] Filed: Sep. 5, 1984

[30] Foreign Application Priority Data

Sep. 8, 1983 [JP] Japan .................. 58-165520

[51] Int. Cl.$^4$ ............................................. A61B 10/00
[52] U.S. Cl. .................... 128/663; 73/861.25
[58] Field of Search ....................... 128/663; 73/861.25

[56] References Cited

U.S. PATENT DOCUMENTS 4,434,669 3/1984 Roberts et al. .................. 128/663 X
4,541,437 9/1985 Amemiya ............................. 128/663

OTHER PUBLICATIONS

Amemiya, S., European Patent Application 0102733 (publication No.) published Mar. 14, 1984.

Primary Examiner—Kyle L. Howell
Assistant Examiner—Francis J. Jaworski
Attorney, Agent, or Firm—Spencer & Frank

[57] ABSTRACT

An ultrasonic wave blood flow meter comprises a probe which sends to and receives an ultrasonic wave reflected with Doppler effect from the blood flow, a detecting circuit for converting a frequency variation of the received reflected wave into a first signal whose amplitude varies with frequency and a second signal whose amplitude is kept constant, and first and second effective-value detecting circuits for obtaining d.c. components of the first and second signals. A level discrimination circuit is further provided for discriminating the level of the d.c. component detected by the second effective-value detecting circuit. First and second sensitivity-variable amplifiers are also provided for varying their sensitivities in accordance with the result of the level discrimination circuit. A dividing circuit divides the d.c. component amplified by the first sensitivity-variable amplifier by the d.c. component amplified by the second sensitivity-variable amplifier, and a voltage hold circuit holds the output of the dividing circuit in accordance with the discrimination result of the level discrimination circuit.

4 Claims, 4 Drawing Figures

ULTRASONIC WAVE BLOOD FLOW METER

BACKGROUND OF THE INVENTION

This invention relates to an ultrasonic wave blood flow meter for measuring the flow rate and the flow speed, etc. of blood by depending upon the Doppler effect of the ultrasonic wave signal reflected from the blood flow.

It is well known that, if an ultrasonic wave is radiated and the Doppler effect of the reflected wave is measured, a signal proportional to the flow rate can be obtained. Furthermore, various methods for obtaining the flow speed from a signal proportional to the flow rate have been proposed. A typical example is the so-called arithmetic method. According to this method, the Doppler signal reflected from the fluid is orthogonally or quadrature-phase detected to obtain two signals $V_A$ and $V_B$ with their phases different by 90° from each other. The signal $V_A$ is differentiated and multiplied with the signal $V_B$. The d.c. component of this signal is divided by the d.c. component of $V_B{}^2$. Then, we obtain a voltage proportional to the flow speed.

However, this method has the following defect. The operation accuracy of the currently available divider is expressed as $$E = e/V_I,$$

where $V_I$ is the denominator voltage and e is the standard error. Therefore, if we perform division by using such a divider, the dividing operation error increases in inverse proportion to the voltage $V_B$. Hence, no accurate flow speed is obtained. When $V_B$ is zero, the output of the divider remains undefined. Due to noise of the input signal, a similar result as in the case of a rapid flow may be obtained. Another defect is that the output in the case without flow or the zero level is not defined well.

This invention is intended to solve the abovementioned problems of the prior art. The objective is to provide an ultrasonic blood flow meter which can keep the operating precision of the divider at a value as constant as possible for such various flow rates and yet can give a zero-frequency output in the absence of flow.

SUMMARY OF THE INVENTION

According to the ultrasonic wave blood flow meter provided by this invention, the frequency variation in the Doppler signal received by a probe is converted into a first signal whose amplitude varies with frequency and a second signal whose amplitude is kept constant without regard to frequency. D.c. components of the first and second signals are amplified by two sensitivity-variable amplifiers which switch their sensitivities in accordance with the level of d.c. component of the second signal. Thereafter, the amplified d.c. component of the first signal is divided by that of the second signal. The divided output is held for a prescribed period.

BRIEF DESCRIPTION OF THE DRAWINGS

The present invention will be made apparent from the following detailed description taken in conjunction with the accompanying drawings, in which.

DESCRIPTION OF THE PREFERRED EMBODIMENTS

Figure 1:
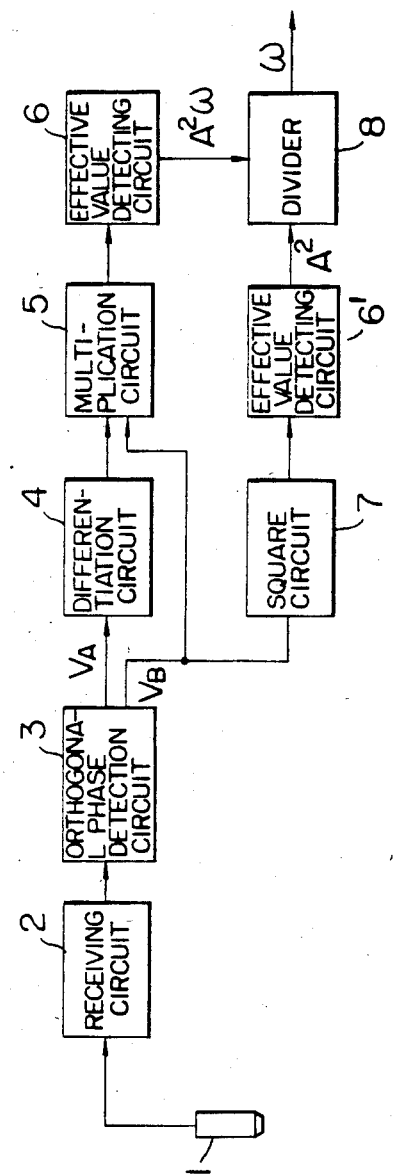
FIG. 1 is a rough block diagram showing a prior-art ultrasonic wave blood flow meter.

Before the explanation of this invention, one example of a prior art ultrasonic wave blood flow meter will be described. In FIG. 1, the ultrasonic wave radiated from a probe 1 is reflected and received by the probe after being subjected to the Doppler effect by the flow of a fluid such as a blood. The wave received by the probe 1 is amplified by a receiving circuit 2 and introduced into an orthogonal-phase detection circuit 3, where signals $V_A$ and $V_B$ with their phases shifted by 90° from each other are obtained. These signals $V_A$ and $V_B$ are related to the blood flow and expressed as follows.

$$V_A = A \sin wt,$$

$$V_B = A \cos wt,$$

where A is the amplitude and w is the angular deviation frequency. The signal $V_A$ is supplied to a differentiator 4 and the frequency variation is converted into a voltage variation $V_A'$ as $$V_A' = A\omega \cos \omega t$$

ps $V_A'$ and $V_B$ are supplied to a multiplication circuit 5 and then to an effective-value detecting circuit (RMS detector) 6. The output of the effective value detecting circuit 6 becomes $A^2\omega$, which is a d.c. voltage proportional to the flow rate. $V_B$ is also supplied to another effective value detecting circuit 6' through a squaring circuit 7. The output of this effective value detecting circuit 6' becomes $A^2$. If the output $A^2\omega$ is divided by the output $A^2$ by a divider 8, we obtain a d.c. output voltage which is proportional to $\omega$ or to the flow speed.

However, since this arrangement has the aforementioned operation error of the divider 8, no accurate flow speed is obtained. When $V_B$ becomes zero, a large error appears.

Figure 2:
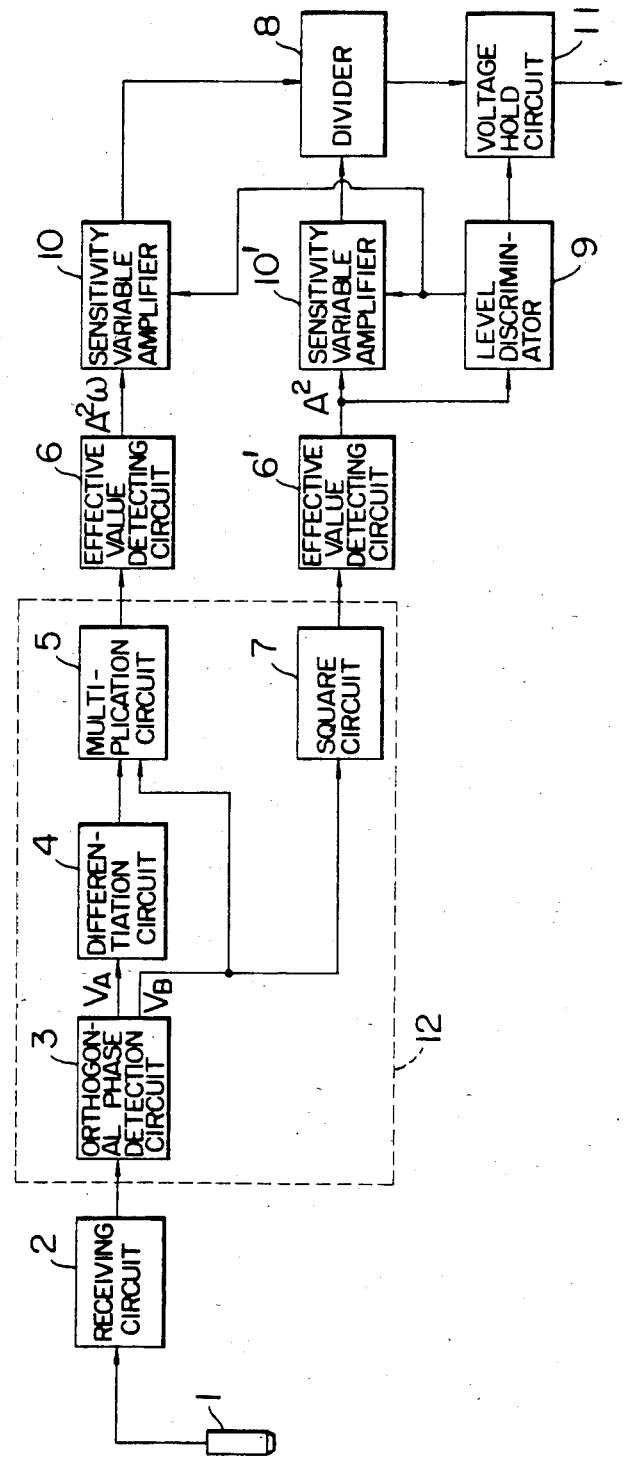
FIG. 2 is a block diagram of an ultrasonic wave blood flow meter according to one embodiment of this invention.

FIG. 2 shows a block diagram showing one embodiment of this invention which solves these defects.

In this figure, 1 denotes a probe, 2 a receiving circuit, 3 an orthogonal-phase detection circuit, 4 a differentiation circuit, 5 a multiplication circuit, 6 and 6' effective-value detecting circuits, and 7 a squaring circuit. The circuit configuration containing these circuits is the same as that of the prior art in FIG. 1. A reflected wave received by the probe 1 is signal-processed (amplification, etc.) by the receiving circuit 2 and converted into signals $V_A$ and $V_B$ with their phases different by 90° in the orthogonal-phase detector 3.

The one signal $V_A$ is differentiated by the differentiator 4 and supplied to the multiplication circuit 5, where it is multiplied with the other signal $V_B$. The output is supplied to an effective-value detecting circuit 6 to obtain an output $A^2\omega$. Signal $V_B$ is passed through a squaring circuit 7 and another effective value detecting circuit 6' to obtain an output $A^2$.

Here, the detecting means comprising the orthogonal-phase detection circuit 3, the differentiation circuit 4, the multiplication circuit 5 and the squaring circuit 7 has a function of separating the signal from the receiving circuit 2 into a signal whose amplitude varies with frequency and a signal whose amplitude is kept constant without regard to the frequency.

Next, the output from the effective-value detecting circuit 6' is introduced into a level discriminator 9 to discriminate the output level of the effective-value detecting circuit 6' and indicate a sensitivity to sensitivity-variable amplifiers 10 and 10' such that the operation error of the following divider 8 can be small. The output $A^2\omega$ of the effective-value detecting circuit 6 and the output $A^2$ of the effective-value detecting circuit 6' are sent to the divider 8 after the sensitivities of the sensitivity-variable amplifiers 10 and 10' are adjusted according to the indication of the level discriminator 9. Through division of the output $A^2\omega$ by the output $A^2$, a d.c. voltage proportional to $\omega$ is obtained. This output is supplied to a voltage hold circuit 11, where an output is generated in accordance with the discrimination result of the level discriminator 9. Thus, the speed of the direction of flow are measured. The voltage hold circuit 11 is of such a type that holds the voltage for a prescribed time and thereafter the output decays gradually to zero. The circuit is constituted with a condenser and a switch and is called a sample-hold circuit.

In the above embodiment, when the level discriminator 9 discriminates that the magnitude of the signal from the effective-value detecting circuit 6' is finite (not null), the switch which constitutes the voltage hold circuit 11 is always turned on so that the divided result of the divider 8 is given as an output.

On the other hand, if the level discriminator 9 discriminates that the signal from the effective-value detecting circuit 6' assumes a zero voltage, the switch which constitutes the voltage hold circuit 11 is turned off and a voltage stored in the condenser just before the zero voltage has been detected is given as an output.

In the circuit configuration of this invention, even if the measuring point deviates from the blood vessel and the flow speed drops to zero suddenly, the abnormally large voltage which would appear in the conventional circuit is not obtained, since the output can be compensated by a voltage at a time just before it has dropped to zero.

When the flow speed becomes zero for a long period, zero value is given to the output after a predetermined time. Therefore, no large errors happen even in the absence of flow.

Although in the above embodiment an orthogonal-phase detection circuit 3 is used in the detecting means 12 where the one signal is processed by the differentiator 4 and the multiplication circuit 5 while the other signal is processed by the squaring circuit 7, any detecting means will do as long as it performs the function of separating the output supplied from the receiving circuit 2 into a first signal whose amplitude varies with frequency and a second signal whose amplitude is kept constant without regard to frequency.

Figure 3:
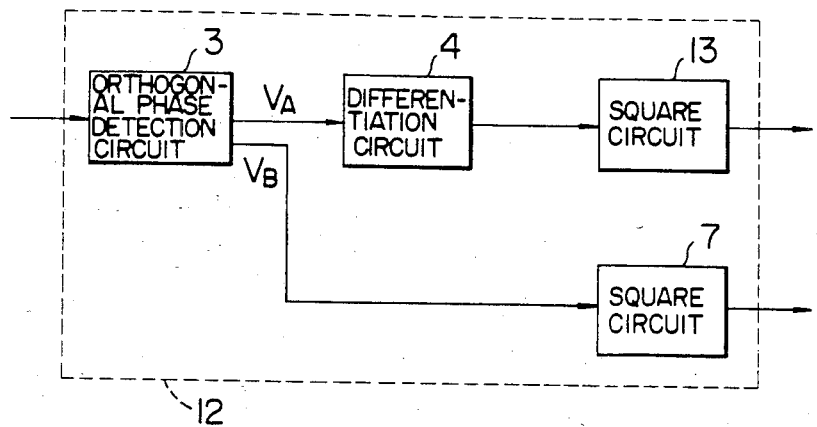
FIG. 3 and FIG. 4 are block diagrams showing another constitution of a detecting means of this invention. In these figures, the same reference numerals are used to denote like parts.
Figure 4:
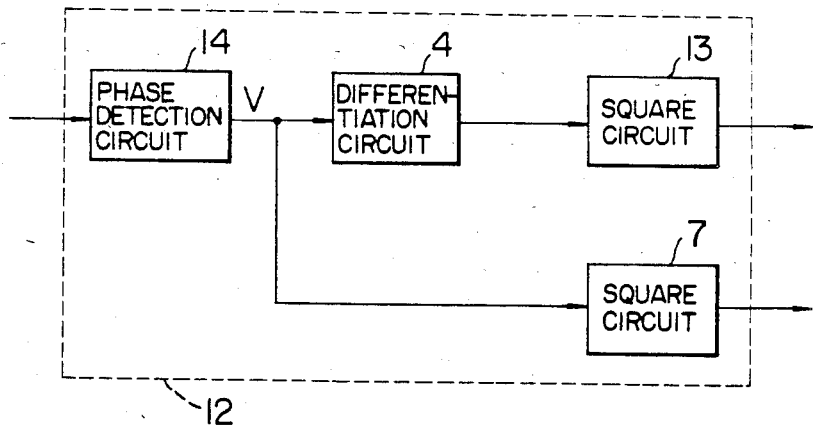

For example, arrangements as shown in FIGS. 3 and 4 work as the detecting means 12.

In FIG. 3, the output from the preceding receiving circuit is supplied to an orthogonal-phase detecting circuit 3, where signals $V_A$ and $V_B$ with the phases different by 90° from each other are generated. The one signal is differentiated by a differentiator circuit 4 and multiplied by itself in a squaring circuit 13 to become a signal whose amplitude varies with frequency. The other signal $V_B$ is multiplied by itself in a squaring circuit 7 to become a signal with a constant amplitude. Thereafter, the same signal processing as in the embodiment of FIG. 2 is performed to obtain the flow speed.

In FIG. 4, the output from the preceding circuit is introduced into a phase detection circuit 14. The output V is passed through a differentiation circuit 4 and a squaring circuit 13 to obtain a signal whose amplitude varies with frequency. The output V is passed to another squaring circuit 7 to obtain a signal with a constant amplitude. Thereafter, the same signal processing as in the embodiment of FIG. 2 is performed to obtain the flow speed.

Both embodiments of FIGS. 3 and 4 have the same effect as that of FIG. 2.

As described above, the present invention provides an ultrasonic wave blood flow meter characterized by comprising a probe which sends and receives an ultrasonic wave at a suitable angle with respect to the blood flow; detecting means for converting a frequency variation of the reflected wave due to the Doppler effect which is received by said probe into a first signal whose amplitude varies with the frequency and a second signal whose amplitude is constant without regard to the frequency; first and second effective-value detecting means for detecting d.c. components of said first and second signals obtained by said detecting means; level discrimination means for discriminating level of the d.c. component detected by said second effective-value detecting means; first and second sensitivity-variable amplification means for varying their sensitivities in accordance with the result of said level discrimination means; dividing means for dividing the d.c. component detected by said first-effective value detecting means and amplified by said first sensitivity-variable amplification means, by the d.c. component detected and amplified by said second sensitivity-variable amplification means; and hold means for holding the output of said dividing means in accordance with the discrimination result of said level discrimination means. The flow speed of blood can be measured always accurately without regard to the level of the reflected ultrasonic wave. Even in the case without flow, the measured result does not become indeterminate and no large errors appear.

We claim:

1. An ultrasonic flow meter for measuring the rate of flow of a fluid comprising
   probe means for sending and receiving an ultrasonic signal which impinges on said fluid and is reflected therefrom;
   detecting means coupled to said probe means for converting frequency variations in said reflected ultrasonic signal due to the Doppler effect into a first signal having an amplitude which varies with frequency and a second signal having an amplitude which is constant and independent of frequency, each of said first and second signals having a d.c. component;
   first and second effective-value detecting means coupled to said detecting means, said first and second effective-value detecting means detecting the d.c. components of said first and second signals respectively;
   level discrimination means coupled to the output of said second effective-value detecting means, said level discrimination means determining the magnitude of the d.c. component of said second signal;
   first and second sensitivity-variable amplification means coupled to the outputs of said first and second effective-value detecting means respectively and to the output of said level discrimination means, the sensitivity of said first and second amplification means being varied in accordance with the output of said level discrimination means;

dividing means coupled to the outputs of said first and second sensitivity-variable amplification means, said dividing means dividing the d.c. component detected by said first effective-value detecting means and amplified by said first sensitivity-variable amplification means by the d.c. component detected by said second effective-value detecting means and amplified by said second sensitivity-variable amplification means; and hold means coupled to the outputs of said dividing means and said level discrimination means for holding the output of said divider means in accordance with the output of said level discrimination means.

2. An ultrasonic flow meter according to claim 1, wherein said detecting means comprises an orthogonal phase detection circuit having first and second outputs and an input coupled to said probe means, the signals generated at said first and second outputs having a 90° phase difference; a differentiation circuit coupled to the first output of said orthogonal phase detection circuit; a multiplication circuit coupled to the second output of said phase detection circuit and to the output of said differentiation circuit, said multiplication circuit multiplying the output of said second orthogonal phase detection circuit and the output of said differentiation circuit to form the product of the two signals; and a squaring circuit for squaring the second output of said orthogonal phase detection circuit.

3. An ultrasonic flow meter for measuring the rate of flow of a fluid comprising probe means for sending and receiving an ultrasonic signal which impinges on said fluid and is reflected therefrom;

detecting means coupled to said probe means for converting frequency variations in reflected ultrasonic signal due to the Doppler effect into a first signal having an amplitude which varies with frequency and a second signal having an amplitude which is constant and independent of frequency, each of said first and second signals having a d.c. component, said detecting means comprising an orthogonal phase detection circuit having first and second outputs and an input coupled to said probe means, the signals generated at said first and second outputs having a 90° phase difference;

a differentiation circuit coupled to the first output of said orthogonal phase detection circuit; and first and second squaring circuits, said first squaring circuit being coupled to the output of said differentiation circuit and said second squaring circuit being coupled to the second output of said orthogonal phase detection circuit;

first and second effective-value detecting means coupled to said detecting means, said first and second effective-value detecting means detecting the d.c. components of said first and second signals respectively;

level discrimination means coupled to the output of said second effective-value detecting means, said level discrimination means determining the magnitude of the d.c. component of said second signal;

first and second sensitivity-variable amplification means coupled to the outputs of said first and second effective-value detecting means respectively and to the output of said level discrimination means, the sensitivity of said first and second amplification means being varied in accordance with the output of said level discrimination means;

dividing means coupled to the outputs of said first and second sensitivity-variable amplification means, said dividing means dividing the d.c. component detected by said first effective-value detecting means and amplified by said first sensitivity-variable amplification means by the d.c. component detected by said second effective-value detecting means and amplified by said second sensitivity-variable amplification means; and hold means coupled to the outputs of said dividing means and said level discrimination means for holding the output of said divider means in accordance with the output of said level discrimination means.

4. An ultrasonic flow meter for measuring the rate of flow of a fluid comprising probe means for sending and receiving an ultrasonic signal which impinges on said fluid and is reflected therefrom;

detecting means coupled to said probe means for converting frequency variations in said reflected ultrasonic signal due to the Doppler effect into a first signal having an amplitude which varies with frequency and a second signal having an amplitude which is constant and independent of frequency, each of said first and second signals having a d.c. component, said detecting means comprising a phase detection circuit having an input coupled to said probe means;

a differentiation circuit coupled to the output of said phase detection circuit; and first and second squaring circuits, said first squaring circuit being coupled to the output of said differentiation circuit and said second squaring circuit being coupled to the output of second phase detection circuit;

first and second effective-value detecting means coupled to said detecting means, said first and second effective-value detecting means detecting the d.c. components of said first and second signals respectively;

level discrimination means coupled to the output of said second effective-value detecting means, said level discrimination means determining the magnitude of the d.c. component of said second signal;

first and second sensitivity-variable amplification means coupled to the outputs of said first and second effective-value detecting means respectively and to the output of said level discrimination means, the sensitivity of said first and second amplification means being varied in accordance with the output of said level discrimination means;

dividing means coupled to the outputs of said first and second sensitivity-variable amplification means, said dividing means dividing the d.c. component detected by said first effective-value detecting means and amplified by said first sensitivity-variable amplification means by the d.c. component detected by said second effective-value detecting means and amplified by said second sensitivity-variable amplification means; and hold means coupled to the outputs of said dividing means and said level discrimination means for holding the output of said divider means in accordance with the output of said level discrimination means.

* * * * *